(12) United States Patent
De Loose et al.

(10) Patent No.: US 6,379,816 B1
(45) Date of Patent: Apr. 30, 2002

(54) LAMINATED METAL STRUCTURE

(75) Inventors: Boudewijn De Loose, Ghent; Ronny Losfeld, Waregem, both of (BE)

(73) Assignee: N.V. Bekaert S.A., Zwevegen (BE)

( * ) Notice: Subject to any disclaimer, the term of this patent is extended or adjusted under 35 U.S.C. 154(b) by 0 days.

(21) Appl. No.: 09/446,842

(22) PCT Filed: Jun. 22, 1998

(86) PCT No.: PCT/EP98/04042

§ 371 Date: Dec. 29, 1998

§ 102(e) Date: Dec. 29, 1998

(87) PCT Pub. No.: WO99/01245

PCT Pub. Date: Jan. 14, 1999

(30) Foreign Application Priority Data

Jun. 30, 1997 (BE) ............................................. 9700559

(51) Int. Cl.⁷ ............................. B32B 1/08; B32B 15/14
(52) U.S. Cl. .................... 428/608; 165/134.1; 165/181; 623/12; 228/212
(58) Field of Search ................................ 428/608, 586, 428/605, 613; 228/143, 173.4, 173.5, 212; 419/9, 24; 165/134.1, 181; 623/12

(56) References Cited

U.S. PATENT DOCUMENTS

| | | | |
|---|---|---|---|
| 3,379,000 A | 4/1968 | Webber et al. ................. 57/139 |
| 3,505,038 A | 4/1970 | Luksch et al. .............. 29/183.5 |
| 3,852,045 A | 12/1974 | Wheeler et al. ............... 29/182 |
| 4,699,637 A | * 10/1987 | Iniotakis et al. .............. 55/158 |
| 4,810,587 A | * 3/1989 | Losfeld et al. .............. 428/549 |
| 4,930,199 A | 6/1990 | Yanagisawa ................. 29/4.51 |
| 5,098,795 A | * 3/1992 | Webb et al. ................. 428/594 |
| 5,679,441 A | * 10/1997 | Saelens et al. .............. 428/198 |

FOREIGN PATENT DOCUMENTS

| | | |
|---|---|---|
| EP | 0 367 354 | 11/1989 |
| GB | 2 183 256 | 6/1987 |
| GB | 2 184 458 | 6/1987 |
| GB | 2 244 719 | 12/1991 |
| WO | 97/04152 | 2/1997 |

OTHER PUBLICATIONS

Paquay, Y.C.G.J., Katholieke Universiteit Nijmegen (NL), *Dacron® versus titanium*, Chapter 4, pp. 76–77, (1996) No month.

* cited by examiner

Primary Examiner—John J. Zimmerman
(74) Attorney, Agent, or Firm—Foley & Lardner

(57) ABSTRACT

Laminated metal structure includes a radially outer component and a radially inner component concentrically interconnected with each other. The radially outer component has a porosity of at least 80% and the radially inner component is a radially impermeable strength element such as a metal foil. The metal structure can be used in a continuous ambulant peritoneal dialysis treatment for anchoring a catheter in the human body.

17 Claims, 2 Drawing Sheets

LAMINATED METAL STRUCTURE

This application is the National Stage entry in the United States of International Application PCT/EP98/04042, filed Jun. 22, 1998.

FIELD OF THE INVENTION

The present invention relates to a laminated sintered metal structure, a method for the manufacture thereof and, more particularly, a medical application therefor.

BACKGROUND OF THE INVENTION

Many applications require metal elements, e.g. tubular metal elements, which are porous and yet possess sufficient strength.

Use of a porous flat metal fibre web, sintered or not, is known in various fields of application, e.g. for burners and filters. However, a structure obtained through the winding up of such fibre web has insufficient strength for many applications. In addition, it is disadvantageous for many applications that the core of the tubular element is not sealed off from the casing or, in other words, that the tube wall is radially porous.

In U.S. Pat. No. 3,505,038 it is disclosed how a tubular filter element can be manufactured by combining a metal fibre web, sintered or not, with a metal wire net.

SUMMARY OF THE INVENTION

It is an object of the present invention to provide a simple sintered metal structure which has a porous outer wall yet sufficient mechanical strength, and whereby the total wall of the structure is impermeable in the radial direction for the fluids contained in the tube. It is another object of the present invention to provide a method for the manufacture of such a metal structure.

According to a first aspect of the present invention, there is provided a laminated or layered metal structure including a radially outer component and a radially inner component concentrically interconnected with each other. The radially outer component has a porosity of at least 80% and may be composed of sintered metal fibres. The radially inner component is a radially impermeable element, which gives strength to the metal structure and may be a metal foil or a thin metal tube or pipe. The sintered metal fibres give the required porosity to the structure whereas the metal foil gives the impermeability and the required strength to the structure.

Both components can be made of any metal or metal alloy whatever. Examples are steel, stainless steel or titanium.

The radially outer component contains metal fibres that can be made by abrading the upper edge of a rolled metal foil, so-called Bekinit fibres, as described in U.S. Pat. No. 4,930,199, or using the bundled drawing technique, as described, e.g., in the patent U.S. Pat. No. 3,379,000. The metal fibres have an equivalent diameter ranging between 2 $\mu$m and 150 $\mu$m, preferably ranging between 40 $\mu$m and 80 $\mu$m. The equivalent diameter of a fibre is the diameter of an imaginary round fibre having the same cross-section as that of the real fibre concerned.

The metal fibres are then processed to form a contiguous porous fibre layer, for example in the form of a nonwoven web, a knitted, woven or wound fabric or mesh, or in the form of helicoidally and diagonally cross-wound metal fibre filaments.

For specific applications, the metal structure is a tubular structure and can be provided with longitudinal anchoring or reinforcing ribs along the outer wall, which, among other things, would enhance its mechanical strength. Transverse anchoring or reinforcing ribs can also be provided around the outside of the tubular structure. Both the longitudinal ribs and the transversal ribs can be of a sintered metal fibre construction, e.g. a sintered steel, stainless steel or titanium fibre construction.

The coated tubular structure according to the present invention can be made of completely bio-inert titanium, thus making the structure exceptionally useful for medical applications. An example of this will be discussed hereunder.

In a preferable embodiment of the present invention, the metal structure has the form of a frustum of a cone. As will be explained hereinafter, such a form allows to have better sintered bonds between the individual steel fibres or steel filaments.

According to a second aspect of the present invention, there is provided a method of manufacturing a metal structure according to the first aspect of the present invention. For an embodiment of the metal structure where the radially outer component is a sintered nonwoven web, the method of manufacturing comprises the following steps:
   (a) wrapping a metal foil around a core;
   (b) wrapping a metal web around the metal foil;
   (c) clamping the foil-web structure obtained in (b) in a mould;
   d) sintering the clamped structure in a furnace.

For an embodiment with two or more longitudinal ribs on the outer surface, the method of manufacturing comprises the following steps:
   (a) wrapping a metal foil around a core;
   (b) wrapping a metal web around the metal foil;
   (c) clamping the foil-web structure obtained in (b) in a mould with two or more longitudinal slits down the inner wall;
   (d) sintering the clamped structure in a furnace.

According to the third aspect of the present invention, there is provided a use of a metal structure according to the first aspect of the invention as anchorage for foreign bodies implanted in an organic tissue. More particularly, there is provided the use of such a metal structure in continuous ambulant peritoneal dialysis (CAPD) treatment for anchoring a catheter in a human body.

According to a fourth aspect of the present invention, there is provided the use of a metal structure according to the first aspect of the present invention as a heat exchanger.

BRIEF DESCRIPTION OF THE DRAWINGS

The present invention will now be explained in more detail referring to the following drawings.

DESCRIPTION OF PREFERRED EMBODIMENTS

Figure 1:
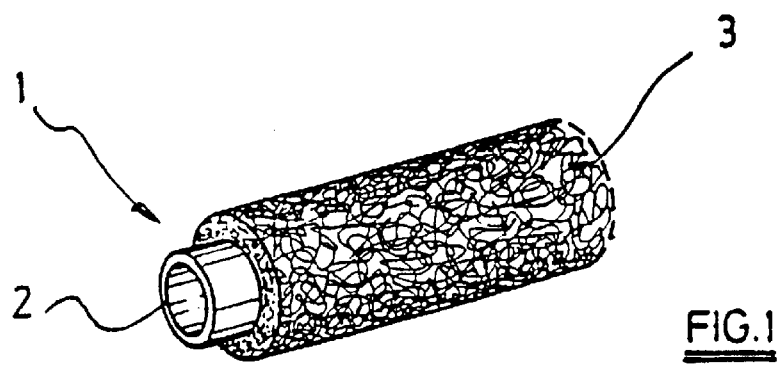
FIG. 1 schematically represents a tubular metal structure according to the present invention, comprising a metal foil surrounded by a metal fibre web.

Referring to FIG. 1, a tubular metal structure 1 according to the first aspect of the present invention has two concentric metal components in the form of a cylinder: a radial inner metal foil 2 and a surrounding component 3 containing metal fibres. Stainless steel or titanium may be preferred according to the intended application.

The metal foil 2 gives the required strength to the tubular metal structure and has a thickness ranging between 20 $\mu$m and 200 $\mu$m. The metal foil 2 also renders the coated metal structure 1 impermeable to fluids and adhesives.

In a preferred embodiment, as shown in FIG. 1, the surrounding component with metal fibres is a sintered metal fibre web 3. The sintered metal fibre web has a porosity greater than 80%, e.g. greater than 85% or greater than 90%.

A method of manufacturing such a laminated tubular structure comprises the following steps:

(a) wrapping the metal foil around a core of a tubular form;

(b) wrapping the metal web around the metal foil;

(c) clamping the foil-web structure obtained in (b) in a mould;

d) sintering the clamped structure in a furnace.

The mould and the core around which the foil is wrapped may be made, e.g., of ceramic material. The wrapping of the metal foil in step (a) is done so that there is a zone of overlapping. During the sintering process (step (d)) the wrapped and partially overlapping metal foil functions as a type of spring and exerts some radially outward pressure on the metal web, which improves the strength of sintered bonds between the individual filaments.

Step (a) may be replaced by fitting a pre-formed tubular metal structure such as a tube or a pipe over a core. In this alternative the advantage of supplemental radially outward pressure is lost, since a tube or a pipe does not function as a spring. This loss of pressure, however, can be compensated by adding some more web material.

The intensity of the sintering treatment in step (d) of the above production method may vary according to the desired strength of the sintered bonds at the points of contact between the metal fibres.

After the sintering treatment in step (d) a supplementary hot isostatic pressing treatment, a so called HIP treatment, may be applied, for example at a pressure of about 1000 bar, at a temperature of about 930° C. and in an environment of nearly pure argon gas (99.9999%). Such a supplementary HIP treatment improves the bonds which have been created between the individual fibres during sintering.

Figure 2:
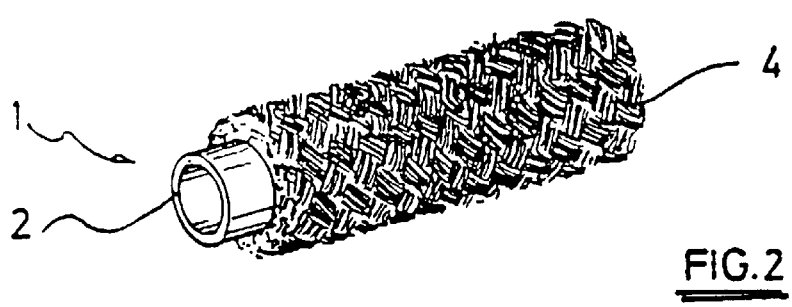
FIG. 2 schematically represents a tubular metal structure comprising a metal foil and a woven layer made of metal filament yarn.

In an alternative embodiment, shown in FIG. 2, the metal structure 1 includes a metal foil 2 and a woven layer 4 of continuous metal fibre bundles (marketed under the trade name Bekinit®).

Figure 3:
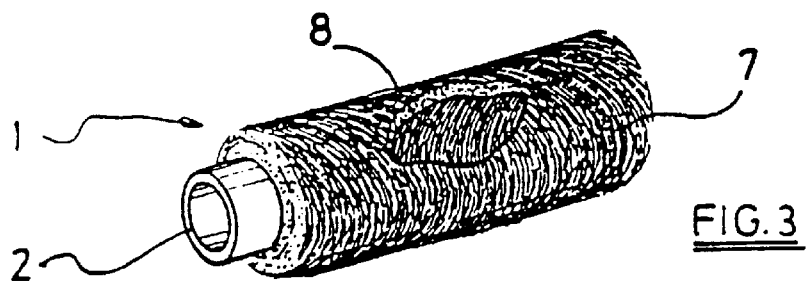
FIG. 3 schematically represents a tubular metal structure comprising a metal foil and a number of helicoidal metal fibre strips wound crosswise over each other.

In a second alternative embodiment, shown in FIG. 3, the metal structure 1 has 2 layers of continuous fibre filaments 7,8 wound diagonally and sintered on to the metal foil 2. Such diagonal winding offers the advantage of a relatively open (porous) structure after sintering.

Figure 4:
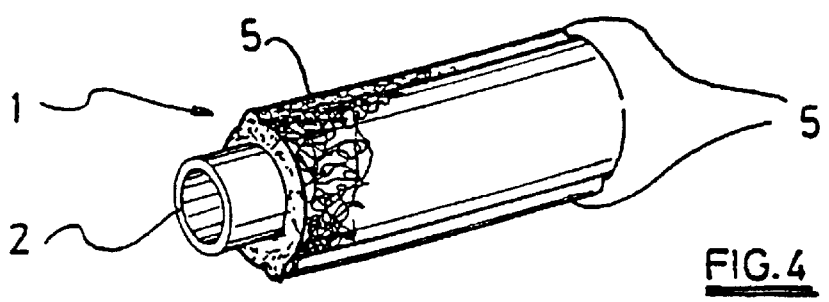
FIG. 4 shows a tubular metal structure that incorporates longitudinal reinforcement ribs.

Depending on the intended applications and, inter alia, on the application explained in a following example, it may be advisable to make the tubular metal structure according to the present invention with two or more longitudinal reinforcing or securing ribs 5 along the outer wall, as shown in FIG. 4.

In a third alternative embodiment, the tubular metal structure according to the invention has an inner metal foil and a knitted tubular metal sleeve, as described in the PCT patent application WO 97/04152 by the applicant. This structure can be manufactured by slipping the knitted fabric over the tubular metal foil supported by means of a mandrel, clamping the knitted fabric in place, then sintering the structure thus obtained in an oven in a vacuum or using a protective inert gas (e.g. hydrogen gas).

EXAMPLE 1

Implant for Securing Foreign Bodies in Organic Tissue

A tubular metal structure according to the first aspect of the present invention can be used as an implant for securing foreign bodies in organic tissue.

Practical examples are the use of the metal structure as a fixing element for a catheter implanted in the human body in continuous ambulant peritoneal dialysis (CAPD) therapy and use of the structure as a fixing element for a central venous catheter (CVC) in the human body.

The CAPD technique allows kidney patients to execute their dialysis independently in discrete, familiar surroundings. This is a major advantage in comparison with the haemodialysis technique, which usually involves a two-day stay in hospital.

In the CAPD technique, the peritoneum acts as a dialysis membrane. A catheter—e.g. of silicon resin—is used to introduce a saline solution into the patient's abdominal cavity. The saline solution purifies the blood naturally by osmosis, the peritoneum acting as a semi-permeable membrane.

EP-B-0 367 354 describes an implant consisting of a percutaneous section and a flat elastic metal fibre mesh. Implanting such an element would likewise require a double surgical operation, as described in Column 4/line 34 to Column 5/line 7. This is a substantial disadvantage that surgeons would prefer to avoid.

A CAPD (silicon) catheter is held in the body by tissue in-growth in one or more porous fixing element(s) mounted concentrically on the catheter, e.g. by means of a biocompatible adhesive. These small elements also form a seal between the skin and the outside world. This is necessary in order to prevent the intrusion of bacteria that can lead to infections and inflammation of the peritoneum.

Still according to the prior art, these elements are usually made of Dacron® (the so-called "Tenckhoff" catheters, commercially available under the trade mark Quinton®, Seattle, USA). This does, however, entail a number of problems. The Dacron® material is not completely biocompatible, which can cause infections, necessitating discontinuation of the CAPD treatment. A further problem is that tissue growth in the element is partially limited as the adhesive used to fix the Dacron® element to the catheter penetrates the Dacron® material radially outwards. This problem is described in Chapter 4, pp. 76, 77 of the doctoral thesis "Titanium fibre mesh anchorage for percutaneous devices applicable for peritoneal dialysis", Paquay Y. C. G. J., Katholieke Universiteit Nijmegen (NL), 1996.

Figure 5:
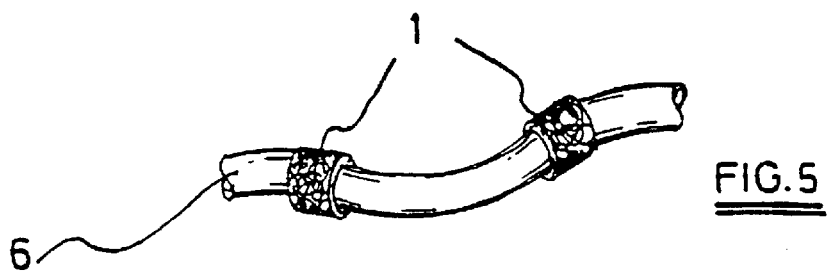
FIG. 5 illustrates how a tubular metal structure according to the present invention can be used as a securing element for a catheter as used in continuous ambulant peritoneal dialysis (CAPD)

Referring to FIG. 5, a tubular metal structure 1 according to the present invention including a titanium foil and a porous titanium fibre web is ideally suited for use as an anchorage for a silicon catheter 6 and removes the disadvantages of the above Dacron® anchorage elements. It also gives the catheter a more solid support.

Titanium is known to be a biologically inert biocompatible material. A coating with a basis of hydroxyl apatite may be applied to improve the biological characteristics of the metal further without impairing its physical properties. The titanium foil also prevents the outward radial penetration of the adhesive on the catheter circumference in the highly porous titanium fibre web, which in no way impairs tissue in-growth in the web. Finally, to obtain a good anchoring of the catheter in the human body, a tubular titanium structure can be used having two or more longitudinal ribs down the length of its outer surface, as described above. These ribs provide a certain mechanical anchorage before tissue in-growth takes place.

Before being used as anchorages for CAPD catheters, tubular titanium structures were made in conformity with the method described earlier, to lengths between 10 mm and 100 mm, having internal diameters of 2 mm to 20 mm and a total wall-thickness ranging from 1 mm to 10 mm.

For practical purposes, a structure is made with a length of 16 mm, an internal diameter of 5 mm and an external diameter of 7.9 mm, with a titanium foil of a thickness of 50 $\mu$m and a titanium fibre web of 614 g/m$^2$ with a basis of titanium fibres having an average equivalent diameter of 50 $\mu$m of a porosity of 90.8%. These anchorage elements are then pressed down on a silicon catheter and glued in place at the desired points.

EXAMPLE 2

Preferable Embodiment in the Form of a Frustum of a Cone

Figure 6:
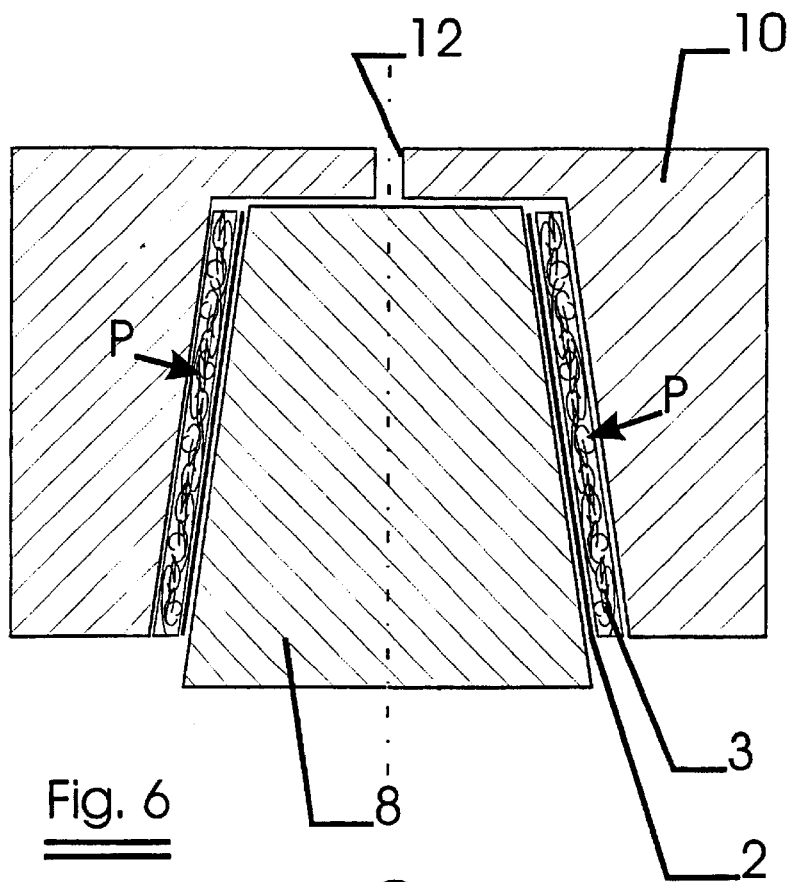
FIG. 6 shows a way of manufacturing a metal structure which has the form of a frustum of a cone.

FIG. 6 illustrates how a preferable embodiment of a metal structure according to a first aspect of the present invention can be made. Such a preferable embodiment has the form of a frustum of a cone. A metal foil 2 is wrapped around a conical core 8 and a metal fibre web 3 is wrapped around the wrapped foil 2. A mould 10 with an internal conical wall is put upon the web-foil structure 2–3 and the whole is put in a sintering furnace. A central hole 12 is provided on top of the mould in order to allow for degassing. The weight of the mould 10 creates a pressure P in the metal fibre web, which would not have been created in case the metal structure is purely cylindrical. Since higher pressures create better bonds between the filaments during sintering, this conical embodiment is likely to have better bonds between the individual steel filaments than in a cylindrical embodiment sintered under the same circumstances.

Figure 7:
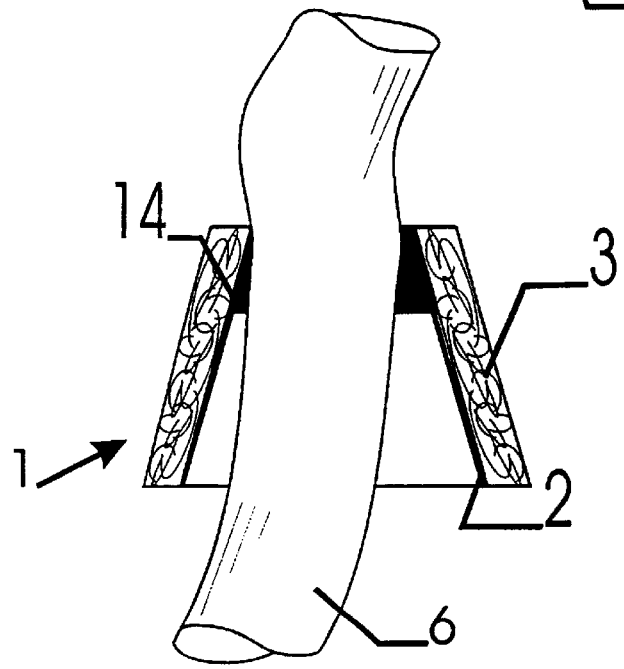
FIG. 7 shows how a metal structure with the form of a frustum of a cone secures a catheter.

FIG. 7 illustrates how a metal structure 1 with the form of a frustum of a cone secures a catheter 6. A catheter 6 with a diameter substantially equal to the smallest diameter of the frusto-conical metal structure is put through the metal structure 1. An adhesive 14 can be easily inserted at the largest diameter of the metal structure 1 in order to secure the catheter 6 to the metal structure at its smallest side. If used as an anchorage for CAPD catheters, such a frusto-conical metal structure may have following dimensions, here given as a matter of example:

height=14 mm
smallest (top) diameter=5 mm
greatest (bottom) diameter=10 mm.

EXAMPLE 3

Heat Exchanger

The tubular metal structure according to the present invention can be used successfully as a heat exchanger. A fluid can be passed through the tubular structure which, for example, can transfer its heat to the fluid surrounding the metal structure. The outer wall of the tubular metal structure is very porous and thus has a large heat-exchange surface, which is very conducive to efficient heat-exchange.

What is claimed is:

1. Laminated metal structure including a radially outer component and a radially inner component concentrically interconnected via sintering with each other, the radially outer component having a porosity of at least 80% and comprising a sintered metal web comprising metal fibers, characterized in that the radially inner component is a radially impermeable metal tube with a wall thickness between 20 $\mu$m and 200 $\mu$m.

2. Metal structure according to claim 1, wherein the radially inner component and the radially outer component are made of steel, stainless steel or titanium.

3. A metal structure according to claim 1 wherein the metal tube is formed by a metal foil.

4. Metal structure according to claim 1, wherein the metal fibers have an equivalent diameter of between 2 $\mu$m and 150 $\mu$m.

5. Metal structure according to claim 1, wherein the metal fibers have an equivalent diameter of between 40 $\mu$m and 80 $\mu$m.

6. Metal structure according to claim 1, wherein the radially outer component is a knitted or woven mesh.

7. Metal structure according to claim 1, wherein the radially outer component has a number of helicoidally and diagonally cross-wound metal fiber filaments.

8. Metal structure according to claim 1 wherein the metal structure has the form of a frustum of a cone.

9. Laminated metal structure including a radially outer component and a radially inner component concentrically interconnected with each other, the radially outer component having a porosity of at least 80%, characterized in that the radially inner component is a radially impermeable metal tube with a wall thickness between 20 $\mu$m and 200 $\mu$m, wherein the radially outer component is a sintered non-woven metal web.

10. Metal structure according to claim 9, provided with two or more longitudinal ribs along the outer surface.

11. Metal structure according to claim 10, wherein the longitudinal ribs are of a sintered metal fiber construction.

12. Metal structure according to claim 11, wherein the longitudinal ribs are of a sintered steel, stainless steel or titanium fiber construction.

13. Method of manufacturing a metal structure according to claim 9, said method comprising the following steps:
    (a) wrapping a metal foil around a core;
    (b) wrapping the metal web around the metal foil;
    (c) clamping the foil-web structure obtained in (b) in a mould;
    (d) sintering the clamped structure in a furnace.

14. Method of manufacturing a metal structure according to claim 11, said method comprising the following steps:
    (a) wrapping a metal foil around a core;
    (b) wrapping the metal web around the metal foil;
    (c) clamping the foil-web structure obtained in (b) in a mould with two or more longitudinal slits down the inner wall;
    (d) sintering the clamped structure in a furnace.

15. An implant for anchoring foreign bodies in organic tissue comprising a metal structure as in claim 9.

16. An implant for anchoring foreign bodies in organic tissue comprising a metal structure as in claim 15, said implant being a fixed element for a catheter during continuous ambulant peritoneal dialysis.

17. A method for exchanging heat comprising:
    (a) providing a metal structure as in claim 9;
    (b) passing a fluid through the metal structure; and
    (c) transferring heat to or from a fluid surrounding the metal structure.

* * * * *